United States Patent
Weber et al.

(10) Patent No.: US 9,061,127 B2
(45) Date of Patent: Jun. 23, 2015

(54) PROTECTIVE SURFACES FOR DRUG-COATED MEDICAL DEVICES

(75) Inventors: Jan Weber, Maastricht (NL); James Q. Feng, Maple Grove, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 494 days.

(21) Appl. No.: 13/458,291

(22) Filed: Apr. 27, 2012

(65) Prior Publication Data

US 2012/0277843 A1      Nov. 1, 2012

Related U.S. Application Data

(60) Provisional application No. 61/480,678, filed on Apr. 29, 2011.

(51) Int. Cl.
  *A61M 31/00* (2006.01)
  *A61M 25/10* (2013.01)
  (Continued)

(52) U.S. Cl.
  CPC ......... *A61M 25/104* (2013.01); *Y10T 156/1051* (2013.01); *A61F 2/958* (2013.01); *A61F 2002/9583* (2013.01); *A61F 2250/0067* (2013.01); *A61M 25/1002* (2013.01); *A61M 2025/0681* (2013.01); *A61M 2025/1004* (2013.01); *A61M 2025/105* (2013.01);
  (Continued)

(58) Field of Classification Search
  CPC ............... A61M 2025/105; A61M 2025/1086; A61M 2025/0681; A61M 2025/1004; A61M 25/104; A61M 25/1002; A61M 2025/104

USPC ............ 604/103.01, 103.02, 103.05, 103.06, 604/103.07, 103.08, 103.14, 103.13, 509; 623/1.11; 424/422
See application file for complete search history.

(56) References Cited

U.S. PATENT DOCUMENTS

| 4,732,152 A | 3/1988 | Wallsten et al. |
| 4,848,343 A | 7/1989 | Wallsten et al. |
| 4,875,480 A | 10/1989 | Imbert |

(Continued)

FOREIGN PATENT DOCUMENTS

| CN | 101239216 | * | 8/2008 |
| CN | 101239216 A | | 8/2008 |
| WO | 94/15549 A1 | | 7/1994 |

OTHER PUBLICATIONS

P.G. Clem et al., Micropen Printing of Electronic Components, Direct-Write Technologies for Rapid Prototyping Sensors (2002), pp. 229-259.

(Continued)

*Primary Examiner* — Theodore Stigell
(74) *Attorney, Agent, or Firm* — Seager, Tufte & Wickhem, LLC

(57) ABSTRACT

Medical balloons having one or more folds, on which are disposed protective surfaces e.g., protective lines or strips, and at least one therapeutic agent between the lines. The protective surfaces prevent, inhibit, or reduce the contact between therapeutic agent on one area, e.g., a surface area, and an opposing area or therapeutic agent on the opposing area when the balloon is folded. The protective surfaces also prevent, inhibit, or reduce loss of therapeutic agent from the balloon surface as a result of, for example, contact with a medical device during expansion or removal of a protective sheath. Also a medical device delivery system comprising a medical device surrounded by a retractable sheath, wherein protective surfaces are disposed on the sheath.

14 Claims, 4 Drawing Sheets

(51) Int. Cl.
*A61F 2/958* (2013.01)
*A61M 25/06* (2006.01)

(52) U.S. Cl.
CPC .............. *A61M2025/1081* (2013.01); *A61M 2025/1086* (2013.01)

(56) References Cited

U.S. PATENT DOCUMENTS

| | | | |
|---|---|---|---|
| 5,102,402 A * | 4/1992 | Dror et al. | ............ 604/265 |
| 5,147,302 A | 9/1992 | Euteneuer et al. | |
| 5,342,307 A | 8/1994 | Euteneuer et al. | |
| 5,458,572 A | 10/1995 | Campbell et al. | |
| 5,662,703 A | 9/1997 | Yurek et al. | |
| 5,690,644 A | 11/1997 | Yurek et al. | |
| 5,954,740 A | 9/1999 | Ravenscroft et al. | |
| 6,013,055 A | 1/2000 | Bampos et al. | |
| 6,059,813 A | 5/2000 | Vrba et al. | |
| 6,544,278 B1 | 4/2003 | Vrba et al. | |
| 6,942,682 B2 | 9/2005 | Vrba et al. | |
| 7,128,868 B2 | 10/2006 | Eidenschink | |
| 7,306,616 B2 | 12/2007 | Eidenschink et al. | |
| 7,572,625 B2 | 8/2009 | Davis et al. | |
| 7,794,488 B2 | 9/2010 | Vrba et al. | |
| 8,114,049 B2 * | 2/2012 | Freyman et al. | ......... 604/103.08 |
| 2004/0215227 A1 | 10/2004 | McMorrow et al. | |
| 2005/0137617 A1 * | 6/2005 | Kelley et al. | ................. 606/170 |
| 2005/0149082 A1 | 7/2005 | Yee et al. | |
| 2006/0212106 A1 | 9/2006 | Weber et al. | |
| 2009/0054837 A1 | 2/2009 | Von Holst et al. | |
| 2011/0178503 A1 | 7/2011 | Kangas | |

OTHER PUBLICATIONS

K.K.B. Hon et al., Direct Writing Technology: Advances and Developments, CIRP Annals, Manufacturing Technology vol. 57 (2008), pp. 601-620.

Saravanukumar et al., Hydroptropic Cligomer-conjugated Glycol Chitosan as a Carrier of Paclitaxel: Synthesis, Characterization, and in vivo Biodistribution, J. Controlled Release vol. 140 (2009), pp. 210-217.

L. Shaw-Klein, Material Selection When Printing Functional Traces on Medical Devices, European Medical Device Technology (May 1, 2010).

European Patent Office, International Search Report and Written Opinion in International Application No. PCT/US2012/035466, dated Sep. 10, 2012.

European Patent Office, Partial International Search Report in International Application No. PCT/US2012/035466, dated Jul. 20, 2012.

* cited by examiner

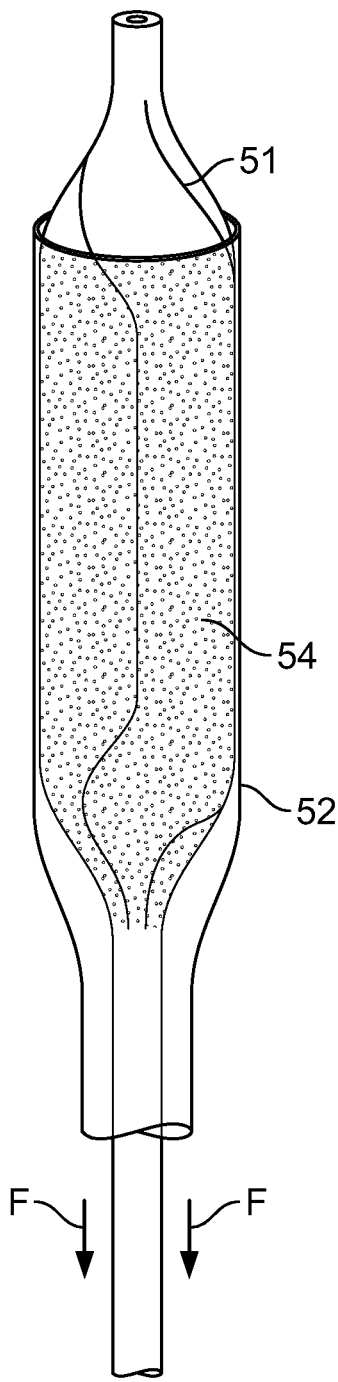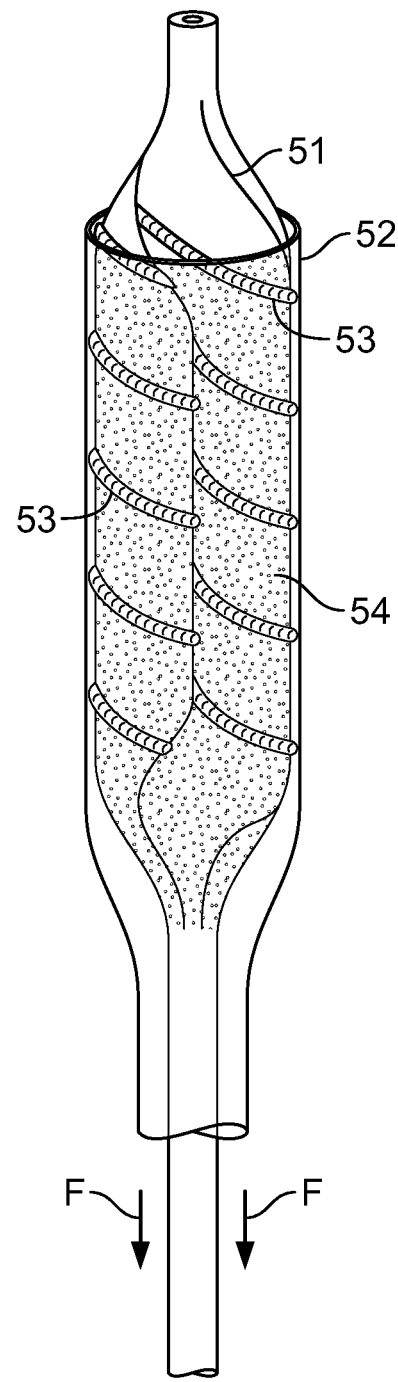
FIG. 4A
(Prior Art)
FIG. 4B

PROTECTIVE SURFACES FOR DRUG-COATED MEDICAL DEVICES

CROSS REFERENCE TO RELATED APPLICATION

The present application claims priority to U.S. provisional application Ser. No. 61/480,678 filed Apr. 29, 2011, the disclosure of which is incorporated herein by reference in its entirety.

TECHNICAL FIELD

The present invention relates to the use of raised or protective surfaces, e.g. protective lines, useful in the delivery of devices and/or therapeutic agents within the body. The protective surfaces can be applied to the surface of expandable medical balloons so as to reduce or prevent the loss of therapeutic agents from the surface of the balloons at the site of delivery. The protective surfaces can also be used to facilitate retraction of sheaths used in the delivery of medical devices within the body.

BACKGROUND

Drug-coated medical balloons are used to deliver a therapeutic agent to a location inside the body, such as to a site within a blood vessel. Medical balloons are used in a wide variety of minimally-invasive or percutaneous medical procedures. Medical balloons having drug coatings may be used to treat diseased portions of blood vessels. Typically, the balloon is inserted through a peripheral blood vessel and then guided via a catheter through the vascular system to the target intravascular site.

The balloon typically is folded to make it more compact and thus facilitate transport to its destination. Once appropriately positioned at its destination, the balloon is inflated, causing it to unfold and press against the surrounding tissue, resulting in release of the drug to the surrounding tissue. There can be substantial loss of drug both during transport of the balloon, to surrounding fluid, during removal of a protective sheath surrounding the balloon, and during unfolding. During removal of a sliding protective sheath, friction between the sheath and therapeutic agent on the balloon surface that is in contact with the sheath can dislodge and cause loss of the therapeutic agent. Also, in the folded state, drug-coated balloon surfaces may be pressed together, causing the drug layer on one surface to come into contact with the drug layer on the opposing surface. When such layers are separated from each other during inflation, the drug layer from one surface can stick to the drug layer on the other surface, resulting in loss of drug into surrounding body fluid and uneven delivery of drug to tissue. Thus the quantity of drug that reaches the intended tissue can be difficult to measure or predict and the application of drug to tissue is non-uniform.

Drug-coated medical balloons and other medical devices are often used with retractable sheaths to deliver the medical device to a location inside the body, such as to a site within a blood vessel. The medical device can be a stent delivered via a stent delivery and dilation catheter system. The stent delivery catheter can employ a retractable sheath such as a rolling retractable sheath that is retracted to release a medical device such as a self-expanding or balloon expandable stent. Sheath removal also can cause drug loss from the surface of the sheathed medical device.

The present invention addresses these needs and deficiencies in its various embodiments as described below.

SUMMARY

The present invention provides medical balloons having one or more folds, on one or more of which are disposed a set of protective surfaces e.g. protective lines or strips and at least one therapeutic agent between the protective surfaces. The protective surfaces prevent, inhibit, or reduce the contact between therapeutic agent on one area, e.g., a surface area, and an opposing area or therapeutic agent on the opposing area when the balloon is folded, relative to the contact that would occur in the absence of protective surfaces. This reduces the loss of therapeutic agent that otherwise would occur during balloon inflation in the absence of protective surfaces. The protective surfaces also prevent, inhibit, or reduce loss of therapeutic agent from the balloon surface as a result of, for example, contact with a medical device during expansion or crimping of the device or during removal of a protective sheath. The protective surfaces also can help to secure a stent on a balloon.

The invention also provides a medical device delivery system comprising a medical device surrounded by a retractable sheath, wherein protective surfaces, e.g. lines or strips are disposed on the sheath such that, during retraction of the sheath, the protective surfaces on the moving part of the sheath slide against the protective surfaces on the stationary part of the sheath, resulting in less friction than would be produced in the absence of the protective surfaces.

Thus, in one embodiment, the present invention provides a medical balloon comprising at least one fold that brings a first area, or surface area, of the balloon into opposition with a second area of the balloon, wherein disposed on the first area is a first set of protective surfaces and between said protective surfaces are one or more layers of a first therapeutic agent. In this embodiment, there may also be disposed on the second area a second set of protective surfaces and further there may be between said second set of protective surfaces one or more layers of a second therapeutic agent, which may be the same as or different from the first therapeutic agent, wherein the protective surfaces are placed in positions such that, when the balloon is folded, at least one protective surface of the first set of protective surfaces is brought into contact with at least one protective surface of the second set of protective surfaces, and further wherein the layer of first therapeutic agent has a height not exceeding the height of any protective surface adjacent to it, and the layer of second therapeutic agent has a height not exceeding the height of any protective surface adjacent to it.

In one embodiment, the protective surfaces of the first set are of about the same height as each other and the protective surfaces of the second set are of about the same height as each other. In one embodiment, some or all of the protective surfaces are protective lines. In a further preferred embodiment, the first set of protective surfaces and the second set of protective surfaces each comprise at least two parallel protective lines and, when the balloon is folded such that the first area is brought into opposition with the second area, the parallel protective lines of the first protective surface are not parallel to the parallel protective lines of the second protective surface and preferably form or intersect at an angle of between about 20° and about 90°. In a further preferred embodiment, all of the protective surfaces of the first set are parallel protective lines and all of the protective surfaces of the second set are parallel protective lines.

In another embodiment, the present invention provides a medical device comprising a catheter and the above-described medical balloon in any of the above-described embodiments. In a preferred embodiment, the medical device further comprises a retractable sheath.

In another embodiment, the present invention provides a method of treating a condition comprising delivering a therapeutic agent to a target site, wherein the therapeutic agent is transported to the target site by the above-described medical balloon. In preferred embodiments, the condition is restenosis.

The invention further provides a method of preparing a balloon for use in delivering a therapeutic agent to a target site, comprising:
a) applying a first set of parallel protective lines to a first balloon area and a second set of parallel protective lines to a second balloon area,
b) applying a first composition comprising a first therapeutic agent so as to place the first therapeutic agent between the protective lines of the first set,
c) applying a second composition comprising a second therapeutic agent so as to place the second therapeutic agent between the protective lines of the second set,
d) drying the balloons so as to cause the solution to evaporate, and
e) folding the balloon so as to cause the first balloon area to come into opposition with the second balloon area such that the areas overlap,
wherein in the folded state the protective lines of the first set are not parallel to the protective lines of the second set and wherein the height of the first protective surfaces is greater than the height of the dried first composition and the height of the second protective surfaces is greater than the height of the dried second composition.

The present invention further provides a medical device delivery system for implantation of a medical device comprising a catheter having proximal and distal ends; a medical device having proximal and distal ends, the medical device being in a delivery configuration wherein the medical device has a reduced radius along its entire axial length; a retractable sheath for retaining the medical device in the delivery configuration and for deploying the medical device; a retraction device for retracting the retractable sheath, the retraction device comprising a connecting member, one end of which connects to the retractable sheath, wherein the surfaces of the retractable sheath that slide against one another during retraction have protective surfaces at least partially disposed in an orientation that is neither parallel to nor perpendicular to the longitudinal axis of the sheath. In a preferred embodiment, the protective surfaces are protective lines. In a preferred embodiment, some or all of the protective lines are disposed in a spiral pattern. In a preferred embodiment, the medical device is a stent.

BRIEF DESCRIPTION OF THE DRAWINGS

FIG. 1A shows the catheter device with the balloon in an inflated state. FIG. 1B shows an enlarged view of two areas of the balloon being folded toward each other and the relative orientation of the protective and therapeutic agent layers on the two areas. FIG. 1C shows an end-on view of part of a folded balloon, in which protective lines contact each other and therapeutic agent layers do not contact each other.

FIGS. 2A and 2B show a conventional covering and FIGS. 2C and 2D show a covering according to an embodiment of the present invention.

FIGS. 4A-4B show a drug-eluting medical balloon with a covering prior to the covering's removal. FIG. 4A shows a conventional drug-eluting medical balloon and FIG. 4B shows a drug-eluting medical balloon according to an embodiment of the present invention.

DETAILED DESCRIPTION

Catheter devices of the present invention use an expandable balloon for delivering a therapeutic agent to a target site in the body. The balloon is designed to be insertable in the body via a catheter. The therapeutic agent can be associated with the balloon in any of various ways, as further described below. Any of various mechanisms conventionally used for the delivery, actuation, or expansion (e.g., by inflation) of balloon catheter devices may be used in the present invention. The balloon catheter may be, for example, an angioplasty catheter, stent delivery catheter, inflation catheter, and/or perfusion catheter. The catheter devices of the present invention may be used in conjunction with other drug delivery devices, such as stents.

The balloon has one or more folds. The folds may be oriented in any of various ways on the balloon, so long as such folds bring two areas of the balloon into opposition with each other. The folds may be made by any of the methods known in the art, including but not limited to methods described in U.S. Pat. No. 5,342,307 (Enteneuer et al.), U.S. Pat. No. 5,147,302 (Enteneuer et al.), U.S. Pat. No. 5,458,572 (Campbell et al.), U.S. Pat. No. 5,954,740 (Ravenscroft et al.), U.S. Pat. No. 6,013,055 (Bampos et al.), U.S. Pat. No. 7,128,868 (Eidenschink), or U.S. Pat. No. 7,306,616 (Eidenschink et al.), 2004/0215227 (McMorrow et al.), which are all incorporated by reference herein.

Figure 1A:
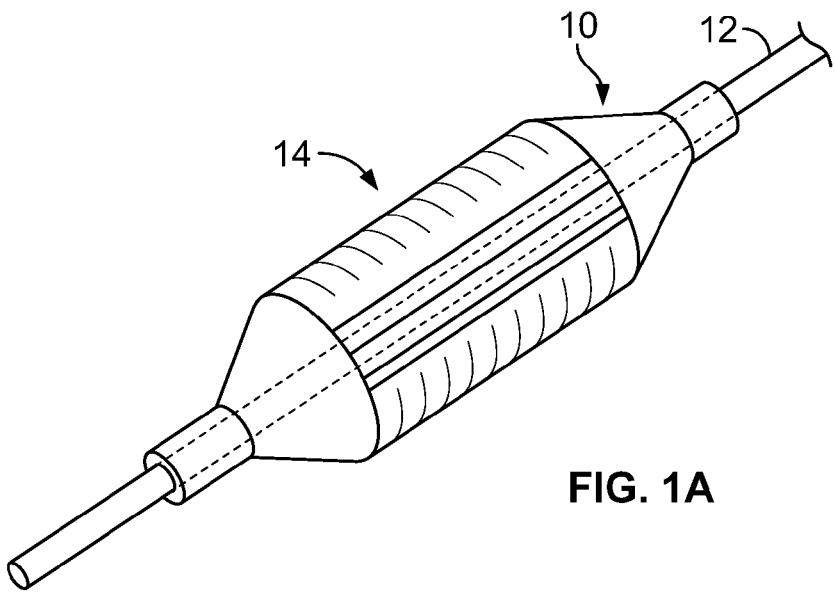
FIGS. 1A-1C show a catheter device according to an embodiment of the present invention.
Figure 1B:
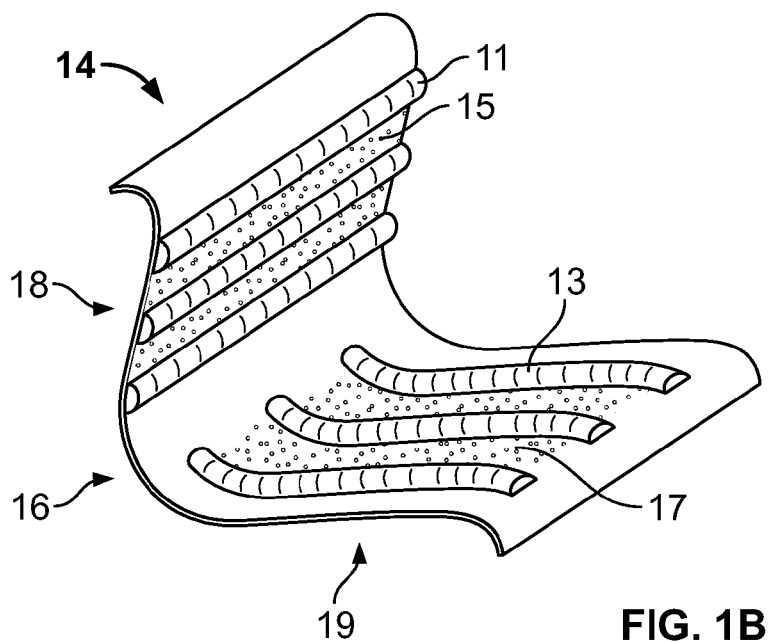
Figure 1C:
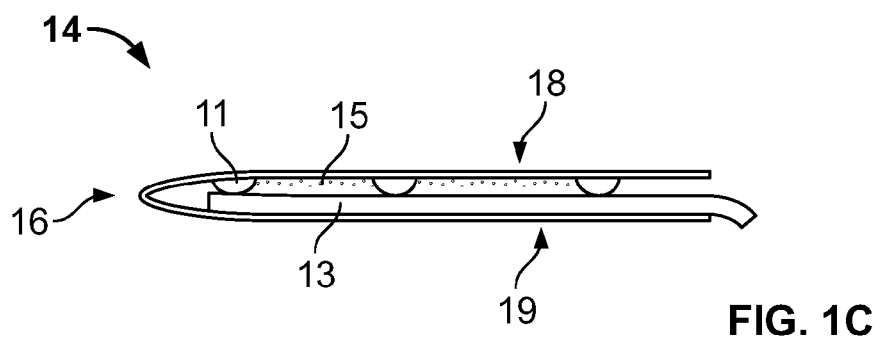

As the balloon is expanded (e.g., by inflation), the folds are made to open such that therapeutic agent that had been concealed by the flap or flaps formed by the folds is exposed and allowed to be released. For example, referring to the embodiment shown in FIG. 1A, a catheter device 10 comprises a balloon 14 mounted on an elongate shaft 12. Referring to FIG. 1B, balloon 14 has a plurality of folds 16 extending longitudinally parallel to the long axis of balloon 14, which is parallel to the elongate shaft. The folds extend between areas 18 and 19. Area 18 comprises first protective lines 11 and first therapeutic agent layers 15 extending parallel to fold 16. Area 19 comprises second protective lines 13 and second therapeutic agent layers 17 extending circumferentially, perpendicular to fold 16. As shown in the enlarged, cross-section view in FIG. 1B, when balloon 14 is in a partially deflated state, areas 18 and 19 are moved toward a position opposite to each other. Referring to FIG. 1C, an end-on view, areas 18 and 19 are folded together such that they are in opposition to each other. In this configuration, first protective lines 11 contact second protective lines 13. The height of first therapeutic agent layers 15 is less than that of first protective lines 11 such that first therapeutic agent layers 15 do not contact second protective lines 13 or second therapeutic agent layers 17 (not shown in FIG. 1C) on opposing area 19. Similarly, the height of second therapeutic agent layers 17 (not shown in FIG. 1C) is less than that of second protective lines 13 such that second therapeutic agent layers 17 do not contact first protective lines 11 or first therapeutic agent layers 15 on opposing area 18.

In operation, balloon 14 is inserted into the body via a catheter. At the target site, balloon 14 is inflated as shown in FIG. 1B, and becomes fully inflated as shown in FIG. 1C, causing areas 18 and 19 to separate and exposing first and second therapeutic agent layers 15 and 17 for release at the target site. Because protecting lines 11 and 13 reduce, inhibit, or prevent altogether contact between therapeutic agent layers 15 and 17 in the folded state, these therapeutic agent layers remain largely or completely intact when areas 18 and 19 are separated from each other and balloon 14 unfolds during inflation.

In certain embodiments, the balloon is designed such that the folds open when the balloon reaches a certain pressure. In certain embodiments, when the balloon is inflated and as the folds open, the folds form a protruding structure that projects outwardly from the main body of the balloon.

Medical devices of the present invention may also include a vascular stent mounted on the balloon. The vascular stent may be any of those known in the art, including those with or without coatings that elute a therapeutic agent. The stent may also be biostable, bioerodable, or biodegradable. In those circumstances where a balloon of the present invention having protective lines and one or more therapeutic agents disposed between the protective lines is paired with or used in conjunction with a stent, for example, when the balloon is used to expand a stent, the protective lines provide the additional advantage of improved securement of the stent. That is, the stent is better held in position relative to the balloon than it would be in the absence of the protective lines. In such circumstances, the protective lines also provide the advantage of reducing the amount of drug lost during expansion of the stent relative to the amount of drug that would be lost during expansion in the absence of protective lines. In the absence of protective lines, as a balloon unfolds and expands a stent, material (e.g. therapeutic agent on the surface of the balloon) between the stent and the balloon is scraped away as the balloon presses with significant force against the stent. Protective lines prevent contact between such material and the stent, thus averting loss of the material.

The balloons of the present invention may also be coated in whole or in part, in one or more layers, with any suitable coating or combination of coatings known to those of skill in the art, such as those described in U.S. Pat. Pub. No. 2006/0212106, which is incorporated herein by reference. Such a coating, for example, may comprise a low-molecular weight carbohydrate, such as mannitol. The carbohydrate may be a separate coating or be blended with the therapeutic agent. Such a coating may also comprise a radiocontrast agent (ionic or non-ionic), such as iopromide, iopamidol, iopentol, ioversol, ioxilan, iotrolan, iodixanol, and ioxaglate. The contrast agent may be a separate coating or be blended with the therapeutic agent.

The therapeutic agent used in the present invention may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, bone marrow cells, and smooth muscle cells. Other therapeutic agents that may be used in the present invention include those listed in U.S. Pat. No. 7,572,625 (Davis et al., "Medical devices coated with drug carrier macromolecules"), which is incorporated by reference herein. Any of the therapeutic agents may be combined to the extent such combination is biologically compatible. Further, the therapeutic agent may be used in its free form or as a salt, hydrate or other solvate and can be amorphous, crystalline, or part of a co-crystal. The therapeutic agent, e.g. paclitaxel, can also be delivered in nanoparticle form alone or with a carrier, for example as described by Saravanukumar et al., J. Controlled Release 140: 210-17 (2009), incorporated herein by reference, describing paclitaxel as carried by a glycol-chitosan conjugate. All these forms may be used in the invention described herein.

In one embodiment, the present invention provides a medical balloon comprising at least one fold that brings a first area of the balloon into opposition with a second area of the balloon, wherein disposed on the first area is a first set of parallel protective surfaces, e.g. lines and, between the first protective surfaces, layers of a first therapeutic agent(s), and, optionally also disposed on the second area is a second set of parallel protective surfaces and, between the second protective surfaces, layers of a second therapeutic agent(s), which may be the same as or different from the first therapeutic agent(s), wherein the protective surfaces of the first set may be parallel or not parallel to the protective surfaces of the second set, and further wherein the layers of therapeutic agents do not exceed in height the protective surfaces adjacent thereto. In a preferred embodiment, the protective surfaces of the first set and the protective surfaces of the second set, when in opposition to each other, form or intersect at an angle of between about 20° and about 90°, such as an angle of about 20°, about 30°, about 45°, about 60°, about 75°, or about 90°. When the parallel protective surfaces of the first set are parallel to the parallel protective surfaces of the second set, the fold that brings the first set of parallel protective surfaces into opposition with the second set of parallel protective surfaces preferably is neither parallel to nor perpendicular to the protective surfaces, and further intersects the parallel lines at an angle between about 15° and about 75°, for example at an angle of about 15°, about 30°, about 45°, about 60°, or about 75°. The therapeutic agent layers on either or both areas may each independently comprise only one therapeutic agent or more than one therapeutic agent. In one embodiment, the therapeutic agents are independently selected from paclitaxel, sirolimus (rapamycin), tacrolimus, everolimus, biolimus, and zotarolimus, or a combination thereof.

Suitable material from which the balloons may be prepared include any known or future developed polymer, for example, a polymeric material, such as a polyether block amide, for example a high durometer PEBAX®, such as PEBAX® 7233, 7033 or 6333 or NYLON 12®. Examples of other polymeric materials from which the balloon may be formed include polyethylene, HYTREL®, polyester, polyurethane, ABS (acrylonitrile-butadiene-styrene) block copolymer, ABS/Nylon blends, ABS/polycarbonate blends and combinations thereof, styrene-acrylonitrile block copolymers, other acrylonitrile copolymers, polyacrylamide, polyacrylates, polyacrylsulfones polyester/polycaprolactone blends, polyetheretherketone (PEEK), polyethersulfone (PES), polyetherimide (PEI), polyetherketone (PEK), polymethylpentene, polyphenylene ether, polyphenylene sulfide, polyolefins such as polyethylene and polypropylene, olefin copolymers, such as ethylene-propylene copolymer, ethylene-vinyl acetate copolymers, ethylene-vinyl alcohol copolymers and polyolefin ionomers, polyvinyl chloride, polycaprolactam, N-vinyl-pyrrolidone, polyurethanes and polysiloxanes. An especially suitable family of materials is polyether block amide materials such as PEBAX™ brand polymers. The balloons may also be prepared from a blend of two or more of the above polymers. Preferably the balloons are non-compliant.

In an embodiment of the invention, the balloon material is a polyether block amide. In a preferred embodiment, the balloon is a non-compliant balloon. Preferably, the balloon material has a shore D hardness of about 67 D-70 D. The protective surface, e.g. protective line or strip, can comprise any suitable material that adheres to the balloon, is flexible, and does not stick to itself. Preferably the protective surface material does not stick to itself. Such materials are known to the person of skill in the art and include, for example, polyamides, polyurethanes, and polyethylenes. In a preferred embodiment, the protective surface material comprises a polyether block amide material such as PEBAX™ brand polymers. Preferably the protective surfaces have a shore D hardness about 1-10 D greater than that of the balloon material. For example, for a balloon having a shore D hardness of about 65 D, the protective surfaces have a shore D hardness of about 66-75 D, for example a hardness of about 66, 67, 68, 69, 70, 71, 72, 73, 74, or 75 D, preferably about 67-70 D. The protective surfaces can contain metal, such as tungsten or barium sulfate. Preferably the balloon is folded to have two or more flaps or wings, such as three, four, five, or six wings.

Materials of which the balloons are made are also suitable for preparing the protective surfaces. In general, a material that is sufficiently flexible that it can follow the balloon folding and that can be made to adhere to the balloon surface by, for example, use of an adhesive may also be suitable for use as a protective surface. For example, a protective material may be formed into an appropriate shape, such as strips or lines, and mounted onto an inflated balloon by use of an appropriate adhesive. The protective surfaces on a balloon may all be made of the same material or of two or more different materials. A set of protective surfaces on an area of a balloon may consist of protective surfaces in the form of lines or strips none of which intersect with each other, e.g. which are parallel to each other.

A protective surface can be affixed to a balloon or an area of a balloon using one or more adhesives. An adhesive may be useful, for example, in the event that a protective surface to be affixed to a balloon is made of the same material as the balloon. Suitable adhesives are known to those of ordinary skill in the art and include, for example, light-curing adhesives, such as a medium flexibility light-curing adhesive such as Dymax's 204-CTH-F adhesive or Dymax's 208-CTH adhesive. The former contains no nonreactive solvents, is made of acrylated urethane, and has a density of 1 g/ml and a viscosity (at 20 rpm) of 500 cP (nominal). When cured, it has a durometer hardness of D55, a tensile at break value of 17 MPa (2500 psi), elongation at break value of 180%, and modulus of elasticity value of 140 MPa (20,000 psi). It is suitable for use in adhesion at least of ABS, PC, PEBA, PET, PI, PS, PU, and PVC. The latter contains no nonreactive solvents, is made of acrylated urethane, and has a density of 1.05 g/ml and a viscosity (at 20 rpm) of 300 cP (nominal). When cured, it has a durometer hardness of D55, a tensile at break value of 10 MPa (1400 psi), elongation at break value of 230%, and modulus of elasticity value of 66 MPa (9,600 psi). It is suitable for use in adhesion at least of ABS, PA, PC, PEBA, PET, PI, PMMA, PS, PU, and PVC and SS.

Suitable carrier materials and solvents for the therapeutic agent layers are those conventionally used in the application of therapeutic agents to balloons, such as those disclosed in U.S. Pat. Pub. No. 2009/0054837, which is incorporated herein by reference.

Application of protective surfaces and therapeutic agents to balloons or to an area of a balloon can be performed sequentially or serially. For example, protective surfaces can be applied to an area followed by application of therapeutic agent layers to the voids between the protective surfaces. Application of the protective surfaces and the therapeutic agent layers can be accomplished using, for example, a direct writing technology such as inkjet or microjet printing, aerosol jet printing (e.g. that of Optomec), pressure driven syringe, syringe-type extrusion (e.g. positive-displacement dispenser (e.g. syringe) (e.g. that of MicroPen)), micro-capillary deposition, or some combination thereof. Such methods are summarized, for example, in L. Shaw-Klein, *Material Selection When Printing Functional Traces on Medical Devices*, European Medical Device Technology 1(5) (May 2010), and described in greater detail in K. K. B. Hon et al., *Direct Writing Technology: Advances and Developments*, CIRP Annals, Manufacturing Technology 57: 601-620 (2008) and P. G. Clem et al., *Micropen Printing of Electronic Components, Direct-Write Technologies for Rapid Prototyping Sensors* 229-259 (2002), all of which are hereby incorporated by reference in their entirety. In this manner the protective surfaces and therapeutic agent can be made in the form of a line or strip.

Regarding the above-described direct-write methods for deposition of the protective surface and therapeutic agent, the material being deposited preferably is in a liquid state for proper dispensing. The liquid formulation can come from solution using solvents, or suspension where the material is in solid particulate form suspended in a carrier liquid (like many inks), or some kind of curable formulation such as UV curable liquid (which before exposed to UV light would stay as liquid and after UV exposure becomes solidified). Thus, the deposited lines or strips are expected to be in a liquid state right after deposition onto the balloon, before the solvents are removed (by drying) or the carrier liquid in suspension is evaporated or the curable material is cured (e.g., by exposing to a UV light).

In the invention illustrated in FIGS. 1A-1D, protective surfaces on one balloon surface are not parallel to protective surfaces on the opposing surface. Preferably the protective surfaces on one balloon surface form an angle with protective surfaces on the opposing surface of at least about 20° to about 90°.

A fold is considered to bring together two areas of a balloon when folding of the balloon along the fold causes two areas of the balloon to be oriented opposite each other.

The invention also provides the use of the protective surfaces described above to reduce the friction caused by removal of a sheath from a sensitive device when such removal entails the sliding of one surface of the sheath against another surface of the sheath, wherein the two surfaces preferably are contiguous with each other. The device may be a medical device, such as but not limited to a stent, filter, or lead. Such a covering ordinarily encloses the device during transport. Such coverings are disclosed, for example, in U.S. Pat. No. 4,732,152 to Wallsten ('152), U.S. Pat. No. 4,848, 343 to Wallsten ('343), U.S. Pat. No. 4,875,480 to Imbert, U.S. Pat. No. 5,662,703 to Yurek et al. ('703), U.S. Pat. No. 5,690,644 to Yurek ('644), U.S. Pat. No. 6,059,813, to Vrba et al. ('813), U.S. Pat. No. 6,544,278 to Vrba et al. ('278), U.S. Pat. No. 6,942,682 to Vrba et al. ('278), U.S. Pat. No. 7,794, 488 to Vrba et al., and WO 94/15549 which are hereby incorporated herein by reference in their entirety. Any sheath the retraction of which entails sliding or dragging of one surface across another surface may be used in the present invention. Also, any device that can be used to retract the sheath, such as those disclosed in the above patents, may be used in the present invention.

The sheath is removed, for example, by axially moving the ends of the covering relative to each other. Removal thus can entail progressive inversion of the covering and simultaneous sliding of the covering against itself. This sliding of one surface against another surface causes friction and thus inhibits removal of the covering. Thus, an embodiment of the present invention is the use of protective surfaces to reduce the friction caused by the removal of the covering. In this aspect of the invention, illustrated in FIGS. 2A-2D and FIGS. 3A-3B (discussed in detail below), the protective surfaces are at least partially disposed in an orientation that is neither parallel to nor perpendicular to the longitudinal axis of the sheath. For example, protective surfaces can be applied to the outside of the sheath in a spiral pattern as illustrated in FIGS. 2C-2D. When the covering is removed, inversion of the covering causes the "inverted" protective surfaces to run in the opposite direction (counter-clockwise vs. clockwise, for example) from the lines on the covering that are still in their original position. As a result, only discrete points of contact between the protective surfaces arise, instead of continuous contact between the surfaces, resulting in less friction and easier removal of the covering. An alternative disposition of protective surfaces in this aspect of the invention is a wave configuration, as illustrated in FIGS. 3A-3B. The skilled artisan will be able to conceive of alternative suitable configurations, which are encompassed within the scope of the present invention.

The sheath can surround all or part of the medical device. The sheath can be a single-wall tube. Refraction of a single-wall sheath entails movement of one end of the sheath towards the other end along the outside of the sheath. The sheath can alternatively comprise two walls, an inner and an outer wall, which are connected at one end such that the outer surface of the inner wall is contiguous with the inner surface of the outer wall.

The use of thermoplastic elastomers such as polyurethane, polyethylene, polyester, polyvinyl chloride, nylon and their block copolymers as well as PEBAX™ polymers is contemplated for a double-walled sheath. Other suitable materials include fluoropolymers, non-compliant polyethylene terephthalate (PET), polyimide and polyolefin copolymers such as SURLYN™ and uniaxially oriented films such as are formed by blow molding. Typically, the materials for use in such sheaths will exhibit high strength even for wall thicknesses as small as $1 \times 10^{-3}$ inches.

Figure 2A:
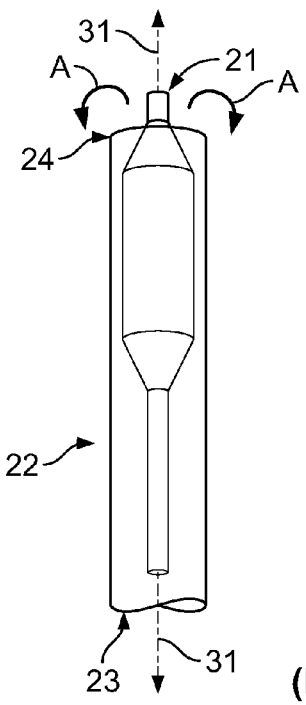
FIGS. 2A-2D show a medical device with a covering prior to the covering's removal and during the covering's removal.
Figure 2B:
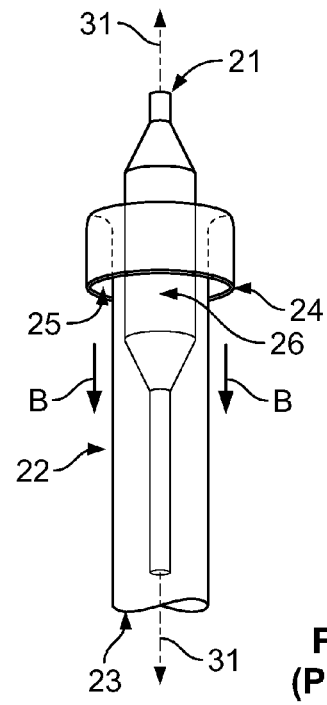
Figure 2C:
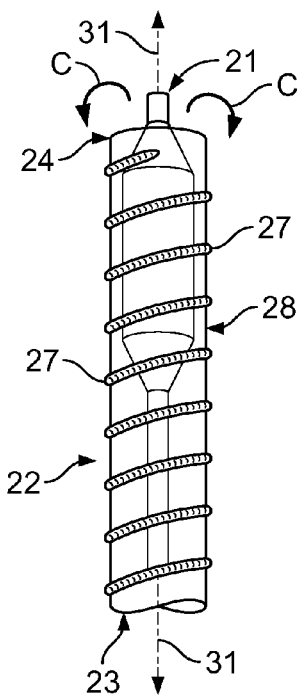
Figure 2D:
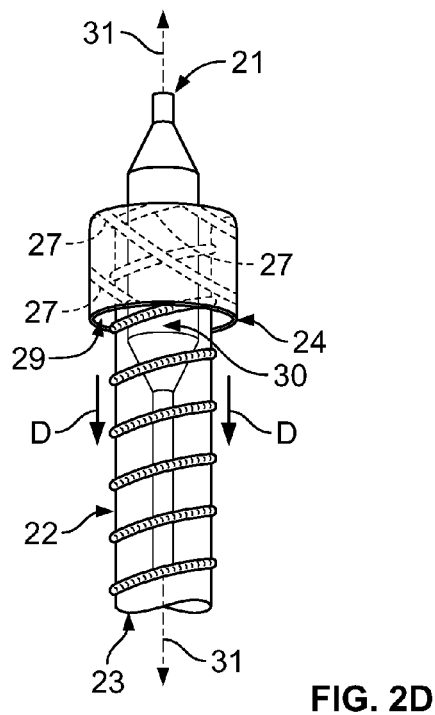
Figure 3A:
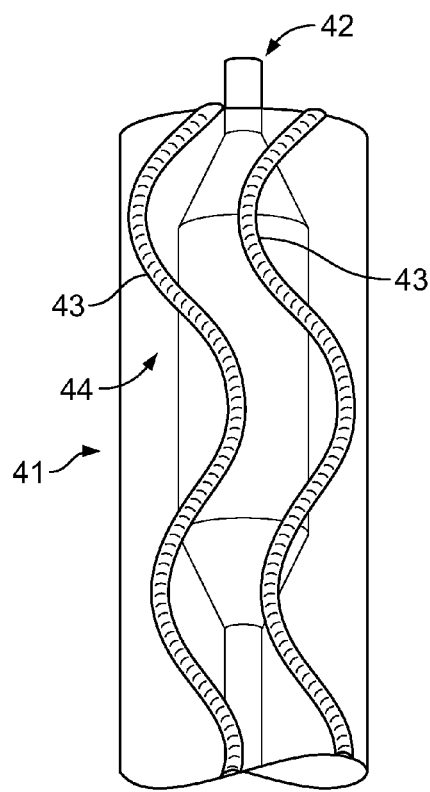
FIGS. 3A-3B show a medical device with a covering according to an embodiment of the present invention prior to the covering's removal and during the covering's removal.
Figure 3B:
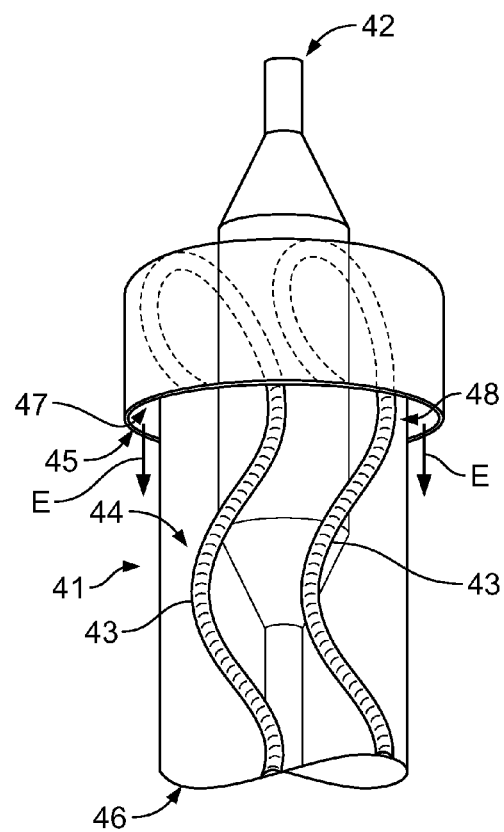

This aspect of the invention is illustrated in FIGS. 2A-2D. FIG. 2A shows a medical device 21 covered by a conventional covering 22 prior to removal of the covering 22. The covering 22 has a proximal end 23, a distal end 24, and a longitudinal axis 31. Distal end 24 will be folded back toward the proximal end 23 as indicated by arrows A to uncover medical device 21. FIG. 2B shows the removal of the covering 22 from the medical device 21. During removal, the covering 22 is folded back at the distal end 24 and dragged toward the proximal end 23, as indicated by arrows B. The folding back of the covering 22 causes friction between the surface in motion 25 and the stationary surface 26. FIG. 2C shows a medical device 21 with a covering 22 according to an embodiment of the invention. The covering 22 has a proximal end 23 and a distal end 24, and a longitudinal axis 31. Protective surfaces 27 have been applied to the exterior 28 of the covering 22 in a spiral pattern. Distal end 24 will be folded back toward the proximal end 23 as indicated by arrows C to uncover medical device 21. FIG. 2D shows the removal of the covering 22 from the medical device 21. During removal, the covering 22 is folded back at the distal end 24 and dragged toward the proximal end 23, as indicated by arrows D. The protective surfaces 27 on the moving surface 29 have an orientation opposite to the protective surfaces 27 on the stationary surface 30. The protective surfaces 27 on the moving surface 29 make discrete regions or points of contact with the protective surfaces 27 on the stationary surface 30 as the covering 22 is removed. The reduction in total area of contact results in a reduction in friction and easier removal of the covering 22.

An alternative embodiment of this aspect of the invention is illustrated in FIGS. 3A-3B. Referring to FIG. 3A, sheath or covering 41 surrounds medical device 42. Protective surfaces 43 are disposed on the exterior surface 44 of sheath 41 in a wave configuration. Referring to FIG. 3B, sheath 41 is shown partially retracted from medical device 42. Distal end 45 is retracted proximally toward proximal end 46, as indicated by arrows E. During refraction, protective surfaces 43 on moving surface 47 make discrete points of contact with protective surfaces 43 on stationary surface 48.

Additionally, where a retractable sheath is used in the delivery of a drug-coated medical balloon, and the sheath is refracted by sliding, protective surfaces as described herein shield the therapeutic agent coating the balloon from the frictional forces caused by such sliding. Instead of a significant quantity of therapeutic agent being in contact with the sheath (those portions of the therapeutic agent located between the balloon folds, for example), the protective surfaces are in contact with the sheath. When the sheath is removed, instead of the sheath sliding against and dislodging the therapeutic agent, resulting in loss of therapeutic agent, the sheath slides against the protective surfaces and the therapeutic agent is retained on the surface of the balloon despite the removal of the sheath. An embodiment of this aspect of the invention is illustrated in FIGS. 4A-4B, as described below.

Referring to FIG. 4A, sheath or covering 52 surrounds medical balloon 51. Therapeutic agent 54 is disposed on the surface of medical balloon 51. Sheath or covering 52 is retracted by sliding off of medical balloon 51, as indicated by arrows F. During retraction, therapeutic agent 54 that is in contact with sheath or covering 52 becomes dislodged from medical balloon 51. Referring to FIG. 4B, sheath or covering 52 surrounds medical balloon 51. Protective surfaces 53 are disposed on the surface of medical balloon 51. Therapeutic agent 54 is disposed on the surface of medical balloon 51 in between protective surfaces 53. Sheath or covering 52 is retracted by sliding off of medical balloon 51, as indicated by arrows F. During retraction, indicated by arrows F, protective surfaces 53 are in contact with sheath or covering 52 and consequently therapeutic agent 54 is not in contact with sheath or covering 52. Refraction of sheath or covering 52 therefore does not dislodge therapeutic agent 54 from medical balloon 51.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A medical balloon comprising at least one fold that brings a first area of the balloon into opposition with a second area of the balloon, wherein:
   - disposed on the first area is a first set of protective surfaces and between said protective surfaces are one or more layers of a first therapeutic agent;
   - disposed on the second area is a second set of protective surfaces and between said protective surfaces are one or more layers of a second therapeutic agent, which may be the same as or different from the first therapeutic agent, and
   - wherein the protective surfaces are placed in positions such that, when the balloon is folded, at least one protective surface of the first set of protective surfaces is brought into contact with at least one protective surface of the second set of protective surfaces, and further wherein the layer of first therapeutic agent has a height not exceeding the height of any protective surface adjacent to it, and the layer of second therapeutic agent has a height not exceeding the height of any protective surface adjacent to it.

2. The medical balloon of claim 1, wherein the protective surfaces of the first set are of about the same height as each other and the protective surfaces of the second set are of about the same height as each other.

3. The medical balloon of claim 2, wherein some or all of the protective surfaces are protective lines.

4. The medical balloon of claim 2, wherein the first protective surfaces and the second protective surfaces each comprise at least two parallel protective lines, and further wherein, when the balloon is folded such that the first area is brought into opposition with the second area, the parallel protective lines of the first protective surface are not parallel with the parallel protective lines of the second protective surface.

5. The medical balloon of claim 4, wherein the parallel protective lines of the first protective surface intersect with the parallel protective lines of the second protective surface at an angle of between about 20° and about 90°.

6. The medical balloon of claim 5, wherein the angle is about 90°.

7. The medical balloon of claim 6, wherein the therapeutic agents are independently selected from paclitaxel, sirolimus (rapamycin), tacrolimus, everolimus, biolimus, and zotarolimus, or a combination thereof.

8. The medical balloon of claim 5, wherein the first protective surfaces and the second protective surfaces comprise a polyether block amide material.

9. The medical balloon of claim 5, wherein the balloon comprises a polyether block amide.

10. The medical balloon of claim 5, wherein the balloon is non-compliant.

11. The medical balloon of claim 10, wherein the protective surfaces have a shore D hardness of about 67 D to about 70 D.

12. A medical device comprising:
   - a catheter, and
   - the medical balloon of claim 4.

13. The medical device of claim 12, further comprising a retractable sheath.

14. A method of treating restenosis comprising delivering a therapeutic agent to a target site, wherein the therapeutic agent is transported to the target site by the medical balloon of claim 4.

* * * * *